(12) United States Patent
Babenko

(10) Patent No.: US 6,277,893 B1
(45) Date of Patent: Aug. 21, 2001

(54) POLYSACCHARIDE AND DIMETHICONE COPOLYOL AS EMULSIFIER FOR COSMETIC COMPOSITIONS

(75) Inventor: Tamara Babenko, Bridgewater, NJ (US)

(73) Assignee: National Starch & Chemical Co. Investment Holding Corporation, Wilmington, DE (US)

( * ) Notice: Subject to any disclaimer, the term of this patent is extended or adjusted under 35 U.S.C. 154(b) by 0 days.

(21) Appl. No.: 09/307,991

(22) Filed: May 10, 1999

(51) Int. Cl.$^7$ ................ B01F 17/00; A61K 7/00

(52) U.S. Cl. ................ 516/67; 516/53; 516/71; 516/72; 516/76; 424/70.13; 514/60; 514/844

(58) Field of Search ................ 516/53, 67, 71, 516/72, 76; 424/70.13, 401; 514/60, 844

(56) References Cited

U.S. PATENT DOCUMENTS

| | | | |
|---|---|---|---|
| 4,698,178 | 10/1987 | Hüttinger et al. | 252/309 |
| 5,162,378 | 11/1992 | Guthauser | 514/785 |
| 5,449,510 | 9/1995 | Gregoire et al. | 424/60 |
| 5,482,704 | 1/1996 | Sweger et al. | 424/70.13 |
| 5,756,122 | 5/1998 | Mackey | 424/402 |
| 5,776,476 | * 7/1998 | Billmers et al. | 424/401 |
| 5,871,756 | * 2/1999 | Jeffcoat et al. | 424/401 |

\* cited by examiner

*Primary Examiner*—Jill Warden
*Assistant Examiner*—Monique T. Cole
(74) *Attorney, Agent, or Firm*—Laurelee A. Duncan; Eugene Zegarella

(57) ABSTRACT

A stable oil-in-water emulsion for use in cosmetic compositions comprising an oil phase which contains the combination of a polysaccharide such as animo-mullticarboxylate starch derivative and a dimethicone copolyol as emulsifier, and a water phase.

22 Claims, No Drawings

POLYSACCHARIDE AND DIMETHICONE COPOLYOL AS EMULSIFIER FOR COSMETIC COMPOSITIONS

BACKGROUND OF THE INVENTION

This invention relates to stable oil-in-water emulsions for use in cosmetic compositions comprising an oil phase which contains the combination of a polysaccharide such as an amino-multicarboxylate starch derivative and a dimethicone copolyol as an emulsifier, and a water phase.

Emulsions are two phase systems consisting of two incompletely miscible liquids, one being dispersed in the other. The most common emulsions are those of oil and water and there are two types of emulsions, namely those in which oil globules are dispersed in water ("oil-in-water" emulsions) and those in which water globules are dispersed in oil ("water-in-oil" emulsions). The present invention involves oil-in-water type emulsions, i.e., where water is the continuous phase and oil is the dispersed or discontinuous phase.

Oil-in-water type emulsions are widely used in cosmetic and dermatolgical compositions or applications, particularly skin, hair and body care compositions, because they help provide aesthetic and appearance characteristics such as gentleness and feel. However, these oil-in-water emulsions often contain well known or classical type surfactants or emulsifying agents which can cause skin irritation or allergic reactions and also may not be compatible with other constituents in the emulsion formulation.

Accordingly, what is desired is an oil-in-water emulsion which is stable and compatible and avoids causing problems such as skin irritations and allergic reactions and are especially useful in cosmetic compositions.

SUMMARY OF THE INVENTION

This invention relates to stable oil-in-water emulsions which are useful in cosmetic compositions and comprises an oil phase that contains the combination of a polysaccharide such as an amino-multicarboxylate starch derivative and a dimethicone copolyol as an emulsifier, and a water phase.

More particularly, this invention is directed to an oil-in-water emulsion comprising an oil phase which contains the combination of:

a) from about 0.1 to 95% by weight, based on the weight of emulsion, of a polysaccharide selected from the group consisting of an amino-multicarboxylate starch derivative, xanthan gum, hydroxyethyl cellulose and hydroxypropyl starch phosphate, the amino-multicarboxylate starch derivative having the following structure:

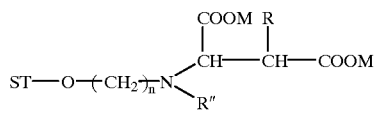

(I)

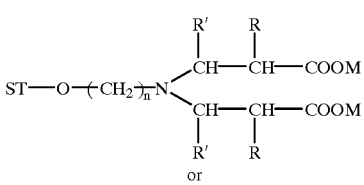

or

-continued

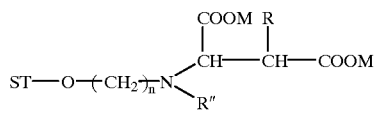

(Ia)

wherein

ST-O represents a starch molecule or a modified starch molecule (wherein the hydrogen of a hydroxy group of an anhydroglucose unit has been replaced as shown);

R is H or $CH_3$;

R' is H, $CH_3$ or COOM

M is a cation selected from the group consisting of H, alkali metal, alkaline earth metal and ammonium:

n is 2 or 3; and

R" is H or alkyl of 1 to 18 carbon atoms; and b) from about 0.1 to 50% by weight, based on the weight of emulsion, of a dimethicone copolyol having the following formula:

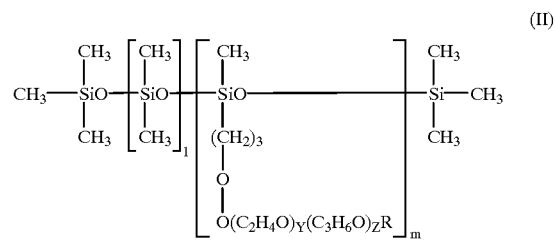

(II)

where I is 0 to 300, m is 1 to 40, y is 4 to 40, z is 0 to 40 and the weight ratio of y:z is from about 100:0 to about 0:100, and R is selected from hydrogen, alkyl, alkoxy and acyl groups having from about 1 to 16 carbon atoms, and a water phase.

This invention also covers a cosmetic composition comprising an oil-in-water emulsion wherein the oil phase contains the combination of a) polysaccharide selected from the group consisting of an amino-multicarboxylate starch derivative, xanthan gum, hydroxyethyl cellulose and hydroxypropyl starch phosphate and b) a dimethicone copolyol as an emulsifier, as defined above and in further detail in this application.

DESCRIPTION OF THE INVENTION

The oil-in-water emulsion of this invention contains the combination of a selected polysaccharide and a dimethicone copolyol as an emulsifier in the oil phase and a water phase. The combination of polysaccharide and dimethicone copolyol when used in the oil phase provides emulsification for the oil-in-water emulsions of this invention and replaces the conventional and known emulsifiers that have been used in typical emulsion compositions. The polysaccharide as used in this invention may be a starch, gum, cellulose or derivative thereof. The starch may be any of several starches, native or converted. Such starches include those derived from any plant source including corn, potato, wheat, tapioca, rice, sago, sorghum, waxy starches such as waxy maize, waxy potato and waxy rice, and high amylose starch such as high amylose corn, i.e., starch having at least 40% and more particularly at least 65% amylose content by weight. Also included are the conversion products derived from any of the former bases such as for example, dextrins prepared by hydrolytic action of acid and/or heat, fluidity or thin boiling starches prepared by enzyme conversion or mild acid hydrolysis and oxidized starches prepared by treatment with oxidants such as sodium hypochlorite. Also included are the derivatized starches such as the hydroxy alkylated or etherified starches, e.g., hydroxypropyl, the esterified starches such as acetylated, cationic and anionic starches, and crosslinked starches. The polysaccharide gums that are useful include xanthan gum, guar gum, locust bean gum, taramind, gum arabic, alginates and gellan. The useful cellulose materials include cellulose and cellulose derivatives such as carboxyalkyl cellulose and hydroxyalkyl cellulose and particularly those having an alkyl of 1 to 4 carbon atoms.

Particularly useful polysaccharide include those selected from the group consisting of an amino-multicarboxylate starch derivative, xanthan gum, hydroxyethyl cellulose and hydroxypropyl starch phosphate. Preferably the polysaccharide is an amino-multicarboxylate starch derivative having one of the structures, I or Ia, as previously described. These starch derivatives can be prepared by reacting starch with selected amino-multicarboxylic acid reagents as described in U.S. Pat. No. 5,482,704 issued to R. W. Sweger et al. on Jan. 6, 1996. The amino-multicarboxylic acid reagents have the following formula:

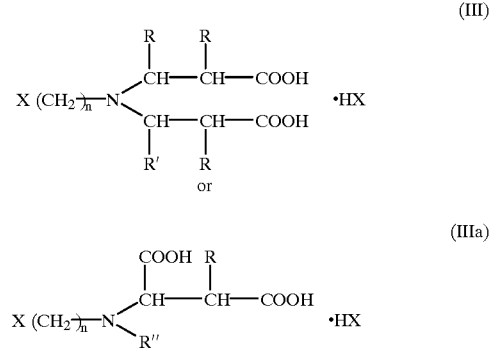

where X is halogen, R is H or $CH_3$, R' is H, $CH_3$ or COOM, n is 2 or 3 and R" is H or alkyl of 1 to 18 carbon atoms.

The reagents III and IIIa as defined above are provided by a Michael reaction between an aminoalcohol and a selected ester containing an activated olefin followed by halogenation. The formation involves reacting the selected multicarboxylate reagent III or IIIa with a starch base in an aqueous medium using either an aqueous slurry or an aqueous dispersion of the starch base. Further description of the preparation of the amino-multicarboxylate starch derivatives can be found in the above noted U.S. Pat. No. 5,482,704 which is incorporated herein by reference.

The applicable starch bases which may be used in preparing the amino-multicarboyxlate starch ether derivatives I and Ia may be derived from any plant source including corn, potato, wheat, rich, sago, tapioca, waxy maize, sorghum, oat, high amylose starch, i.e., starch having amylose content of greater than about 45% by weight such as high amylose corn, etc. Also included are the conversion products derived from any of the latter bases including, for example, dextrins prepared by the hydroyses of acid and/or heat; oxidized starches prepared by treatment with oxidants such as sodium hypochlorite; fluidity or thin-boiling starches prepared by enzyme conversion or mild acid hydrolyses; and derivatized starches such as ethers and esters. Starch esters will undergo hydrolyses when exposed to reaction conditions needed to prepare starch ethers. If mixed starch ethers/esters are desired, it is obvious to those skilled in the art that the ether substituents must be reacted first, followed by esterification. The intermediate starch ether can be directly esterified or isolated and purified prior to esterification. The starch base may be a granular starch or a gelatinized starch, i.e., non-granular starch.

The preferred starch derivatives I and Ia of this invention as described above, are those wherein R, R' and R" are hydrogen, M is hydrogen and n is 2 and more particularly those having the structure I. The starch base is preferably potato starch. Also the starch base and the resulting starch derivatives may be further derivatized or modified with other groups such as cationic groups. Particularly useful cationic starches are the tertiary aminoalkyl starch ethers such as 2-diethylaminoethyl chloride and quaternary ammonium starch ethers such as 2,3-epoxypropyltrimethylammonium chloride.

The dimethicone copolyol of formula II used in this invention and described above is an organopolysiloxane-polyoxyalkylene polymer composition. This polysiloxane polyether copolymer is further identified by the name dimethicone copolyol. This is the name designated by the Cosmetic, Toiletry and Fragrance Association (CTFA) for certain polysiloxane polyether copolymers. It is a commercially available product available from several suppliers including Dow Corning as found in the International Cosmetic Ingredient Dictionary, 6th edition, 1995, published by the CTFA in Washington, D.C. Compositions of this type are further disclosed in U.S. Pat. No. 5,756,112 issued to L. Markey on May 26, 1998 and U.S. Pat. No. 4,698,178 issued to R. Hiitinger et al. on Oct. 6, 1987, both of said patents being incorporated herein by reference. The dimethicone copolyol as defined by formula II may be linear or branched and may be block or random copolymers. Preferably, the dimethicone copolyols are block copolymers having one or more polysiloxane blocks and one or more polyether blocks. Preferably the organopolysiloxane-polyoxyalkylene of formula II will have I of 10 to 40, m of 1 to 10, y of 3 to 30, z of 4 to 30, a weight ratio of y:z of from 100:0 to 35;65 and R is hydrogen or $CH_3$. The molecular weight of the $(C_2H_4O)_y$—$(C_3H_6O)_z$ radical is typically from about 150 to 3000 and R is preferably hydrogen.

The combination of amino-multicarboxylate starch derivative of formula I and Ia or other selected polysaccharide with a dimethicone copolyol of formula II has been found especially useful in providing stable oil-in-water emulsions. These stable emulsions are provided by adding the starch derivative or polysaccharide along with the dimethicone copolyol to the oil phase and then combining it with the aqueous or water phase to form the emulsion. This stable oil-in-water emulsion has been found particularly useful in cosmetic compositions because of their stability as well as the compatibility of the starch derivative and dimethicone copolyol with each other and the various functional additives and ingredients used in such compositions.

The oil phase of the oil-in-water emulsion of this invention will include from about 0.1 to 95% by weight and preferably from about 0.1 to 15% of the amino-multicarboxylate starch derivative or other selected polysaccharide, based on the weight of emulsion. The oil phase will also contain about 0.1 to 50% by weight and preferably from about 0.1 to 10% of dimethicone copolyol, based on the weight of emulsion. Additionally, the oil phase will contain other conventional oily substances, particularly those that are cosmetically acceptable such as oils and waxes. Compounds which may be included in the oil phase are typically mineral, animal and vegetable oils and fats, synthetic esters, fatty acids, aliphatic alcohols, higher fatty alcohols, alkyl amines, waxes, so called mineral fats and oils such as paraffin oil, petrolatum, silicone oils and silicone fats, silanes, steroids and sterols. These oily substances in the oil phase generally comprise from about 0.5 to 75% by weight, based on the weight of emulsion, i.e., excluding the amino-multicarboxylate starch or other polysaccharide and dimethicone copolyol from the oily substances. Also preservatives, vitamins, essential oils and other additives and ingredients as described below can be added to the oil phase.

The water phase of the oil-in-water emulsion will comprise from about 5 to 98% and preferably from about 25 to 90% by weight, based on the weight of the emulsion. This will include water and water soluble components such as alkalies, alkanolamines, polyhydric alcohols and preservatives. Other additives and ingredients as described below can also be added to the water phase.

The oil-in-water emulsion of this invention are particularly useful in cosmetic and pharmaceutical or medicament compositions such as creams, lotions, antiperspirants, make-up products, sunscreens, shampoos and body cleansing products. In formulating the cosmetic compositions, various additives and other ingredients may be included in one or both of the oil and water phases of the emulsions described herein, or they can be added after the emulsion is formed. These additives and other ingredients include emollients, humectants, thickening agents, UV-A and UV-B filter substances, preservatives, dyes, colorants, alpha hydroxy acids, aesthetic enhancers such as starch, perfumes and fragrances, film formers (water proofing agents), hydrophilic or lipophilic active agents, stabilizers, fillers, antioxidants, antiseptics, antifungal, antimicrobial and other medicaments and solvents. Effective amounts of one or more of these and other active and functional ingredients can generally be used and this can total from about 0.001 to 50% by weight of the composition and more particularly from about 0.1 to 15% by weight, based on the weight of the composition.

Preparation of the emulsion compositions of this invention typically involves adding the oil phase components along with the amino-multicarboxylate starch derivative and dimethicone copolyol to one vessel. This oil phase is then heated to about 75 to 90° C. with mixing. Water and other water phase components are combined and heated to about 80° C. and mixed in another vessel. The water phase is then slowly added to the oil phase at 80° C. while mixing. The average pH of the emulsion will range from about 5 to 8.0 and can be adjusted to about 2.5 to 8.5 by the addition of an acid or base. This adjustment can typically be with alpha hydroxy acids and/or beta hydroxy acids, hydrochloric acid or organic/inorganic base. Cosmetic emulsion compositions are prepared in a similar manner by adding the various functional additives and ingredients to the appropriate respective phases.

The following examples further illustrate the embodiments of this invention. In the examples, all parts and percentages are given by weight and all temperatures in degrees Celsius unless otherwise noted. The CEPA potato starch as described in the examples, is modified potato starch and is made and sold by National Starch and Chemical Company under the name Structure Solanace.

EXAMPLE I

This example illustrates the preparation of a cosmetic oil-in-water emulsion composition in accordance with this invention. An oil phase was formulated by combining the oil phase components described below and which included an amino-multicarboxylate potato starch derivative and dimethicone copolyol. The potato starch derivative was prepared by modifying potato starch with 2-chloroethyfaminodipropionic acid (hereinafter referred to as CEPA). This modified CEPA potato starch has the structure of formula I.

The oil phase components were combined and heated to about 75 to 90° C. with mixing. The water phase components were combined and heated to 80° C. and then slowly added to the oil phase while maintaining the temperature at 80° C. for 20–30 minutes with mixing.

|  | % W/W |
|---|---|
| Phase A | |
| Dimethicone | 7.5 |
| Cyclomethicone | 12.5 |
| CEPA potato starch | 2.0 |
| Dimethicone Copolyol | 5.0 |
| Phase B | |
| Deionized water | q.s. to 100 |
| Preservatives | q.s. |

A stable emulsion (at 45° C. for eight weeks) was formed and the composition had good compatibility and rheology as well as aesthetic look and soft feel.

EXAMPLE II

Similar emulsion compositions were prepared as in Example I (Samples B to F) and had the following formulations:

|  | % W/W | | | | |
|---|---|---|---|---|---|
|  | B | C | D | E | F |
| Phase A | | | | | |
| Hydrogenated polyisobutene | 22.0 | — | — | — | — |
| Mineral oil | — | 25.0 | — | — | — |
| $C_{12-15}$ alkyl benzoate | — | — | 25.0 | — | — |
| Isohexadecane | — | — | — | 20.0 | — |
| Caprylic/capric triglyceride | — | — | — | — | 20.0 |
| CEPA potato starch | 2.0 | 2.0 | 2.0 | 2.0 | 2.0 |
| Dimethicone copolyol | 3.0 | 3.0 | 4.0 | 2.0 | 3.0 |
| Phase B | | | | | |
| Deionized water | all q.s. to 100 | | | | |
| Preservatives | all q.s. | | | | |

All of the above cosmetic oil-in-water emulsion compositions were stable, compatible and provided good Theological, aethetic and other functional properties.

EXAMPLE III

Another oil-in-water emulsion composition similar to Example I was prepared using xanthan gum in place of the CEPA modified potato starch. Samples G to I were formulated as follows:

|                          | W/W % |       |      |
|--------------------------|-------|-------|------|
|                          | G     | H     | I    |
| Phase A                  |       |       |      |
| Xanthan gum              | 0.5   | 0.75  | 0.5  |
| Dimethicone copolyol     | 2.0   | 5.0   | 2.0  |
| Hydrogenated polyisobutene | 23.0 | —     | —    |
| Dimethicone              | —     | 7.5   | —    |
| Cyclomethicone           | —     | 12.5  | —    |
| Isohexadecane            | —     | —     | 20.0 |
| Phase B                  |       |       |      |
| all samples had deionized water q.s. to 100 and preservation q.s. | | | |

The cosmetic oil-in-water emulsion compositions G to I all were stable and compatible and had good functional properties.

EXAMPLE IV

Cosmetic oil-in-water emulsion compositions similar to Example I were prepared using hydroxypropyl starch phosphate (Sample J) and hydroxyethylcellulose (Sample K) instead of CEPA modified potato starch. The formulations were as follows:

|                          | W/W % |            |
|--------------------------|-------|------------|
|                          | J     | K          |
| Phase A                  |       |            |
| Hydroxypropyl starch phosphate | 8.0 | —      |
| Hydroxyethylcellulosel   | —     | 0.75       |
| Dimethicone copolyol     | 5.0   | 5.0        |
| Dimethicone              | 7.5   | 7.5        |
| Cyclomethicone           | 12.5  | 12.5       |
| Phase B                  |       |            |
| Deionized water          | q.s. to 100 | q.s. to 100 |
| Preservatives            | q.s.  | q.s.       |

Both compositions (J and K) were stable and compatible and displayed good functional properties making them useful as cosmetic compositions.

EXAMPLE V

Additional oil-in-water emulsion compositions were prepared as in Example I and have the following ingredients:

|                          | W/W % |            |
|--------------------------|-------|------------|
|                          | L     | M          |
| Phase A                  |       |            |
| Dimethicone              | 7.5   | 7.5        |
| Cyclomethicone           | 12.5  | 12.5       |
| Dimethicone copolyol     | 5.0   | 5.0        |
| CEPA potato starch       | 2.0   | 2.0        |
| Phase B                  |       |            |
| Deionized water          | q.s. to 100 | q.s. to 100 |
| Hydroxyethyl cellulose   | 0.35  | —          |
| PEG-7M                   | —     | 0.35       |
| Preservatives            | q.s.  | q.s.       |

Stable emulsions of the above compositions were formed and they had good compatibility as well as aesthetic and soft feel properties.

EXAMPLE VI

Another oil-in-water emulsion was prepared as in Example I and having the following ingredients:

|                          | W/W %       |
|--------------------------|-------------|
| Phase A                  |             |
| Hydrogenated polyisobutene | 22.0      |
| Dimethicone copolyol     | 3.0         |
| Xanthan gum              | 0.5         |
| Hydroxyethyl cellulose   | 0.5         |
| Phase B                  |             |
| Deionized water          | q.s. to 100 |
| Preservatives            | q.s.        |

This formulation provided a stable emulsion with good compatibility, aesthetic and feel properties.

EXAMPLE VII

Another oil-in-water emulsion was prepared as in Example I and having the following ingredients:

|                          | W/W %        |
|--------------------------|--------------|
| Phase A                  |              |
| Dimethicone              | 6.5          |
| Cyclomethicone           | 14.5         |
| Dimethicone copolyol     | 3.0          |
| CEPA potato starch       | 1.35         |
| Xanthan gum              | 0.3          |
| Hydroxyethyl cellulose   | 0.25         |
| Phase B                  |              |
| Deionized water          | q.s. to 100% |
| Magnesium aluminum silicate | 1.0       |
| Preservatives            | q.s.         |

EXAMPLE VIII

A lotion was formed preparing the oil-in-water emulsion as in Example I with the following ingredients:

|                          | % W/W  |
|--------------------------|--------|
| Phase A                  |        |
| Octyl methoxycinnamate   | 7.5    |
| Octyl salicylate         | 5.0    |

-continued

| | % W/W |
|---|---|
| Benzophenore-3 | 3.0 |
| Isoeicosane | 7.0 |
| Cholesterol | 1.0 |
| Cyclomethicone | 4.5 |
| Phenyl trimethicone | 2.6 |
| Dimethicone copolyol | 3.0 |
| CEPA potato starch | 1.25 |
| Xanthan gum | 0.35 |
| Phase B | |
| Deionized water | q.s. to 100% |
| Preservatives | q.s. |

The above prepared lotion was stable and had both good aesthetic look and soft feel characteristics.

EXAMPLE IX

A sunscreen lotion was prepared having the following ingredients. The ingredients of Phase A were combined and heated to 75 to 90° C. while mixing. The water of Phase B was heated to 80° C. and the remaining ingredients added with mixing. Phase B was then slowly added to Phase A with continued mixing for 20 to 30 minutes and maintaining the temperature at 80° C. Phase C was then added with mixing and Phase D ingredients were premixed and added at 45° C.

| | W/W % |
|---|---|
| Phase A | |
| Octyl methoxycinnamate | 7.5 |
| Octyl salicylate | 5.0 |
| Benzophenone-3 | 3.0 |
| Isoeicosane | 7.0 |
| Choesterol | 1.0 |
| Cycomethicone | 4.5 |
| Phenyl Trimethicone | 2.6 |
| Cetearyl Alcohol | 1.25 |
| Dimethicone copoyol | 3.0 |
| CEPA potato starch | 1.4 |
| Xanthan gum | 0.35 |
| Phase B | |
| Deionized water | q.s. to 100% |
| Sodium hydroxide (25%) | 0.9 |
| Acrylate/octylacrylamide Copolymer (Dermacryl 79) | 2.0 |
| Phase C | |
| Preservatives | q.s. |
| Phase D | |
| Propylene glycol | 2.0 |
| Corn starch modified (DryFlo AF) | 2.0 |

The prepared sunscreen lotion was stable and had good aesthetic look and soft feel properties.

What is claimed is:

1. An oil-in-water emulsion comprising an oil phase which contains the combination of a polysaccharide and a dimethicone copolyol, the combination thereof acting as the sold emulsifier, and a water phase.

2. The composition of claim 1 wherein the polysaccharide is a starch, gum, cellulose or derivative thereof.

3. The composition of claim 1 wherein the oil phase comprises from about 0.1 to 95% by weight, based on the weight of emulsion, of the polysaccharide and from about 0.1 to 50% by weight, based on weight of emulsion, of the dimethicone copolyol.

4. The composition of claim 3 wherein the polysaccharide is selected from the group consisting of an amino-multicarboxylate starch derivative, xanthan gum, hydroxyethyl cellulose and hydroxypropyl starch phosphate, the amino-multicarboxylate having one of the following structures:

$$ST-O-(CH_2)_n-N\begin{matrix}CH(R')-CH(R)-COOM \\ CH(R')-CH(R)-COOM\end{matrix} \quad (I)$$

or $$ST-O-(CH_2)_n-N\begin{matrix}CH(COOM)-CH(R)-COOM \\ R''\end{matrix} \quad (Ia)$$

wherein

ST represents a starch molecule or a modified starch molecule (wherein the hydroxy group of an anhydroglucose unit has been replaced as shown);

R is H or $CH_3$;

R' is H, $CH_3$ or COOM

M is a cation selected from the group consisting of H, alkali metal, alkaline earth metal and ammonium:

n is 2 or 3; and

R" is H or alkyl of 1 to 18 carbon atoms; and the dimethicone copolyol having the following formula:

$$CH_3-\underset{CH_3}{\underset{|}{Si}}O-\left[\underset{CH_3}{\underset{|}{Si}}O\right]_l-\left[\underset{\underset{O}{\underset{|}{(CH_2)_3}}}{\underset{|}{Si}}O\right]-\underset{CH_3}{\underset{|}{Si}}-CH_3 \quad (II)$$
$$O(C_2H_4O)_Y(C_3H_6O)_ZR\Big]_m$$

where I is 0 to 200, m is 1 to 40, n is 1 to 100, y is 4 to 40, z is 0 to 40 and the weight ratio of y:z is from about 100:0 to about 0:100, and R is selected from hydrogen, alkyl, alkoxy and acyl groups having from about 1 to 16 carbon atoms.

5. The composition of claim 4 wherein the polysaccharide is the amino multicarboxylate starch derivative of formula I.

6. The composition of claim 5 wherein in the starch derivative of formula I, each R, R' and R" is H, M is H and n is 2.

7. The composition of claim 6 wherein the starch is potato starch.

8. The composition of claim 4 wherein the dimethicone copolyol of formula II has I of 10 to 40, m of 1 to 10, the molecular weight of the $(C_2H_4O)_y-(C_3H_6O)_z$ radical is from about 150 to 3000 and R is hydrogen or $CH_3$.

9. The composition of claim 8 wherein the polysaccharide is the amino-multicarboxylate starch derivative of formula I.

10. The composition of claim 9 wherein in the starch derivative of formula I, each R, R' and R" is H, M is H and n is 2.

11. The composition of claim 10 wherein the starch is potato starch.

12. A cosmetic oil-in-water emulsion composition which comprises an oil phase containing the combination of a polysaccharide and a dimethicone copolyol, the combination thereof acting as the sole emulsifier, and a water phase.

13. The composition of claim 12 wherein the polysaccharide is a starch, gum, cellulose or derivative thereof.

14. The composition of claim 12 wherein the oil phase comprises from about 0.1 to 95% by weight, based on the weight of emulsion, of the polysaccharide and from about 0.1 to 50% by weight, based on the weight of emulsion, of the dimethicone copolyol.

15. The composition of claim 14 wherein the polysaccharide is selected from the group consisting of an amino-multicarboxylate starch derivative, xanthan gum, hydroxyethyl cellulose and hydroxypropyl starch phosphate, the amino-multicarboxylate having one of the following structures:

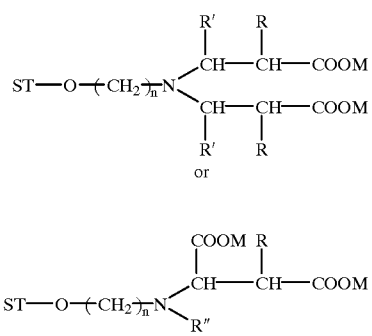

wherein
ST represents a starch molecule or a modified starch molecule (wherein the hydroxy group of an anhydroglucose unit has been replaced as shown);
R is H or $CH_3$;
R' is H, $CH_3$ or COOM
M is a cation selected from the group consisting of H, alkali metal, alkaline earth metal and ammonium:
n is 2 or 3; and
R" is H or alkyl of 1 to 18 carbon atoms; and
the dimethicone copolyol having the following formula:

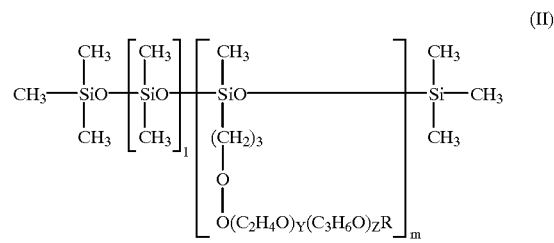

where I is 0 to 200, m is 1 to 40, n is 1 to 100, y is 4 to 40, z is 0 to 40 and the weight ratio of y:z is from about 100:0 to about 0:100, and R is selected from hydrogen, alkyl, alkoxy and acyl groups having from about 1 to 16 carbon atoms.

16. The composition of claim 15 wherein the polysaccharide is the amino-multicarboxylate starch derivative of formula I.

17. The composition of claim 16 wherein in the starch derivative of formula I, each R, R' and R" is H, M is H and n is 2.

18. The composition of claim 17 wherein the starch is potato starch.

19. The composition of claim 15 wherein the dimethicone copolyol of formula II has I of 10 to 40, m of 1 to 10, the molecular weight of the $(C_2H_4O)_y$—$(C_3H_6O)_z$ radical is from about 150 to 3000 and R is hydrogen or $CH_3$.

20. The composition of claim 19 wherein the polysaccharide is the amino-multicarboxylate starch derivative of formula I.

21. The composition of claim 20 wherein in the starch derivative of formula I, each R, R' and R" is H, M is H and n is 2.

22. The composition of claim 21 wherein the starch is potato starch.

* * * * *